United States Patent
Takemoto et al.

(10) Patent No.: US 8,855,262 B2
(45) Date of Patent: Oct. 7, 2014

(54) X-RAY PHOTOGRAPHING DEVICE

(75) Inventors: Terumi Takemoto, Tokyo (JP); Michizo Yamanaka, Tokyo (JP)

(73) Assignee: The Yoshida Dental Mfg. Co. Ltd. (JP)

( * ) Notice: Subject to any disclaimer, the term of this patent is extended or adjusted under 35 U.S.C. 154(b) by 371 days.

(21) Appl. No.: 13/380,154

(22) PCT Filed: Jun. 21, 2010

(86) PCT No.: PCT/JP2010/060424
§ 371 (c)(1), (2), (4) Date: Dec. 22, 2011

(87) PCT Pub. No.: WO2010/150719
PCT Pub. Date: Dec. 29, 2010

(65) Prior Publication Data
US 2012/0093284 A1 Apr. 19, 2012

(30) Foreign Application Priority Data
Jun. 25, 2009 (JP) .................................. 2009-150654

(51) Int. Cl.

| | |
|---|---|
| *A61B 6/14* | (2006.01) |
| *A61B 6/03* | (2006.01) |
| *A61B 6/02* | (2006.01) |
| *A61B 6/00* | (2006.01) |
| *A61B 6/06* | (2006.01) |

(52) U.S. Cl.
CPC ............... *A61B 6/035* (2013.01); *A61B 6/4208* (2013.01); *A61B 6/4452* (2013.01); *A61B 6/06* (2013.01); *A61B 6/4464* (2013.01); *A61B 6/032* (2013.01); *Y02B 90/2692* (2013.01); *A61B 6/587* (2013.01); *A61B 6/4441* (2013.01); *A61B 6/14* (2013.01); *A61B 6/02* (2013.01); *A61B 6/4476* (2013.01)
USPC ............................................ 378/38; 378/197

(58) Field of Classification Search
CPC .......... A61B 6/032; A61B 6/035; A61B 6/14; A61B 6/4233; A61B 6/4441; A61B 6/4464; A61B 6/4452; A61B 6/4405; H05G 1/02
USPC .................................. 378/4, 38, 39, 193, 197
See application file for complete search history.

(56) References Cited

U.S. PATENT DOCUMENTS

2004/0000630 A1    1/2004    Spartiotis et al.

FOREIGN PATENT DOCUMENTS

| EP | 1 491 145 | 12/2004 |
|---|---|---|
| EP | 1 018 941 | 7/2005 |

(Continued)

OTHER PUBLICATIONS

International Search Report for corresponding International Patent Application No. PCT/JP2010/060424 mailed Sep. 14, 2010.

(Continued)

*Primary Examiner* — Jurie Yun
(74) *Attorney, Agent, or Firm* — Merchant & Gould P.C.

(57) ABSTRACT

An X-ray photographing device comprising a turning means for turning an x-ray source and an X-ray sensor around a subject is provided with an arcuate movement means for arcuately moving the X-ray sensor around an arcuate movement center axis, and a control unit. The control unit continuously performs a first photographing step for detecting an X-ray flux while turning the X-ray sensor in a first arcuate movement range around the arcuate movement center axis by the arcuate movement means, a shifting/turning step for shifting/turning an arcuate movement arm around the subject by the turning means, and a shifting/photographing step for detecting the X-ray flux while turning the X-ray sensor in a second arcuate movement range around the arcuate movement center axis by the arcuate movement means in the state shifted from the first arcuate movement range by a very small angle in the shifting/turning step.

10 Claims, 12 Drawing Sheets

(56) References Cited

FOREIGN PATENT DOCUMENTS

| | | |
|---|---|---|
| EP | 2 053 972 | 9/2013 |
| GB | 1 571 489 A | 7/1980 |
| JP | 52-079681 A | 7/1977 |
| JP | 63-021039 A | 1/1988 |
| JP | 10-225455 A | 8/1998 |
| JP | 2004-208754 A | 7/2004 |
| JP | 2006-314774 A | 11/2006 |
| JP | 2006-320347 A | 11/2006 |
| JP | 2008-114056 A | 5/2008 |
| JP | 2009-066305 A | 4/2009 |
| JP | 2009-131656 A | 6/2009 |
| WO | WO 99/17659 | 4/1999 |
| WO | WO 2008/021671 | 2/2008 |
| WO | WO 2009/063974 | 5/2009 |

OTHER PUBLICATIONS

European Search Report for EP Application No. 10 79 2037 mailed Dec. 8, 2013 (9 pages).

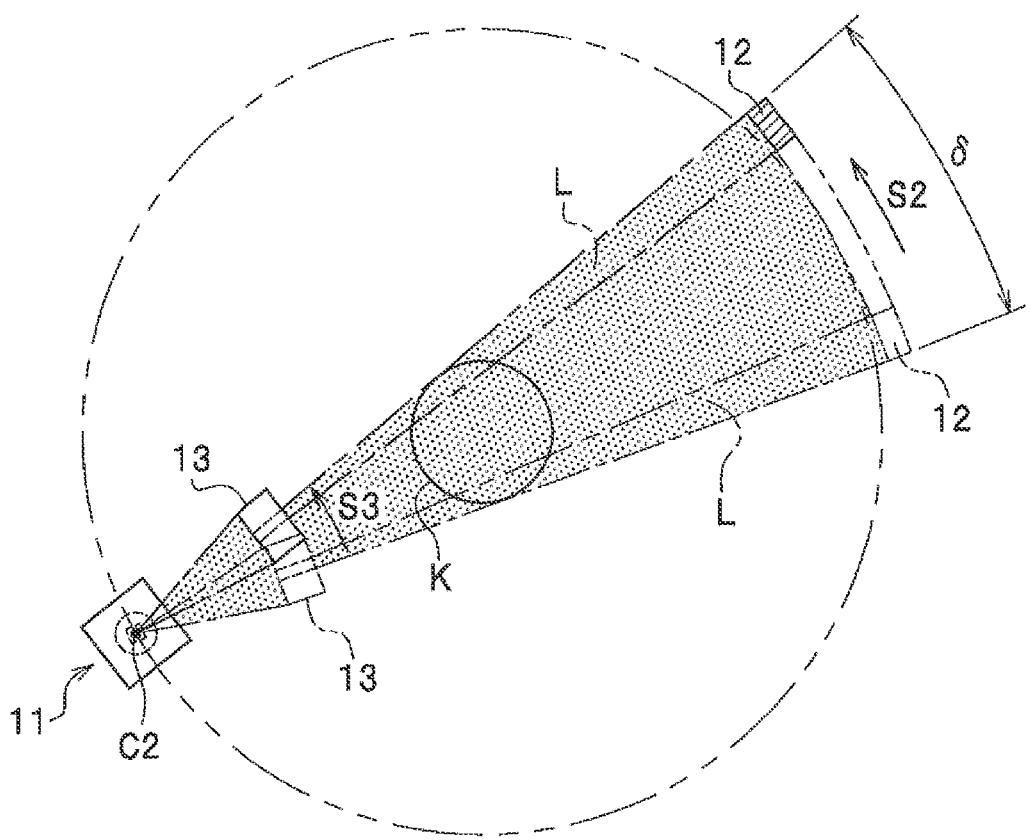

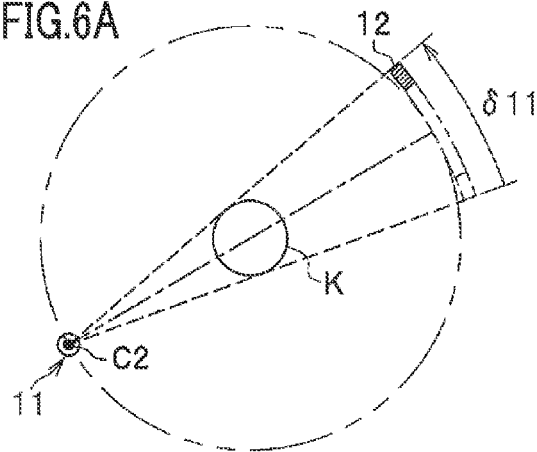
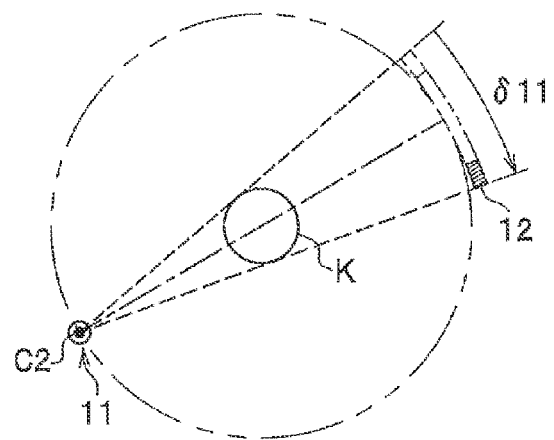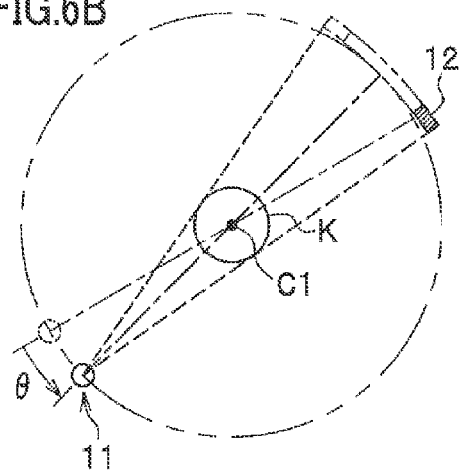
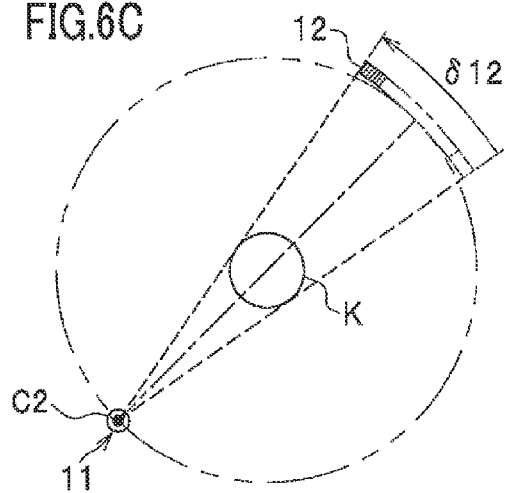

X-RAY PHOTOGRAPHING DEVICE

This application is a National Stage Application of PCT/JP2010/060424, filed 21 Jun. 2010, which claims benefit of Serial No. 2009-150654, filed 25 Jun. 2009 in Japan and which applications are incorporated herein by reference. To the extent appropriate, a claim of priority is made to each of the above disclosed applications.

FIELD OF THE INVENTION

The present invention relates to an X-ray photographing device, and in particular to an X-ray photographing device which can obtain CT (computerized tomography) tomographic images using an inexpensive X-ray photographing means having a relatively narrow rectangular detecting area.

BACKGROUND ART

Conventionally, since a CT photographing device in dental treatment needs a large amount of image data, CT tomographic images are obtained using a two-dimensional sensor having a generally large detecting area. On the other hand, a panoramic photographing device can obtain panoramic tomographic images using a CCD (Charge Coupled Device) sensor having a relatively small rectangular detecting area.

Also, in an X-ray photographing device which can obtain CT tomographic images and panoramic tomographic images by switching between a CT photographing and a panoramic photographing in order to enhance convenience, a two-dimensional sensor having a large detecting area is used (see Patent Literature 1).

PRIOR ART DOCUMENT

Patent Literature

Patent Literature 1: JP 10-225455 A (see FIG. 18)

DISCLOSURE OF THE INVENTION

Problem to be Solved

However, the two-dimensional sensor having the large detecting area which is necessary for the CT photographing is expensive, a processing unit for the image data becomes complicated, and the device becomes expensive as a whole. As a result, the CT photographing device has not become widely used in dental treatment.

Hence, in order to solve the above described problem, it is an object of the present invention to provide an X-ray photographing device which can obtain CT tomographic images using an inexpensive X-ray photographing means having a relatively small rectangular detecting area, and can cut down costs efficiently.

Means for Solving the Problem

In order to solve the above described problem, the present invention provides an X-ray photographing device, comprising: an X-ray source for emitting an X-ray flux to a subject; an X-ray photographing means for detecting the X-ray flux passing through the subject; a supporting member for supporting the X-ray source and the X-ray photographing means; a turning means for turning the supporting member to turn the X-ray source and the X-ray photographing means around the subject; an arcuate movement means for arcuately moving the X-ray photographing means around the subject by turning the X-ray photographing means around an arcuate movement center axis provided on a line joining the subject and the X-ray photographing means; and a control unit for controlling operations of the turning means and the arcuate movement means, wherein the control unit continuously executes a first photographing step of detecting the X-ray flux passing through the subject by the X-ray photographing means while the X-ray photographing means is turned around the arcuate movement center axis within a first arcuate movement range by the arcuate movement means; a shifting/turning step of shifting/turning the supporting member around the subject by the turning means; and a shifting/photographing step of detecting the X-ray flux passing through the subject by the X-ray photographing means while the X-ray photographing means is turned around the arcuate movement center axis within a second arcuate movement range by the arcuate movement means with the supporting member being shifted from the first arcuate movement range by an infinitesimal angle in the shifting/turning step, wherein the shifting/turning step and the shifting/photographing step are further executed sequentially following the shifting/photographing step.

In this way, the present invention behaves as a two-dimensional X-ray photographing means within a range where the X-ray photographing means is arcuately moved by detecting the X-ray flux passing through the subject while the X-ray photographing means is arcuately moved around the subject by turning the arcuate movement means around the arcuate movement center axis.

For this reason, for example, by arcuately moving an X-ray photographing means having a relatively small rectangular detecting area, the X-ray photographing means can behave as a wide-range two-dimensional X-ray photographing means which can detect the X-ray flux within the arcuate movement range.

Also, by scanning the subject while turning the X-ray photographing means which behaves as a wide-range two-dimensional X-ray photographing means around the subject by the turning means, CT tomographic images can be obtained.

In this way, the present invention can cut down costs efficiently by realizing an X-ray photographing device which can obtain CT tomographic images using an inexpensive X-ray photographing means having a relatively small rectangular detecting area.

In the X-ray photographing device according to the present invention, the arcuate movement center axis is preferably provided at a position where the X-ray source is provided.

According to the above structure, by arcuately moving the X-ray photographing means around the X-ray source, the X-ray source is not arcuately moved. As a result, a stable X-ray flux is emitted, and an image fluctuation can be suppressed.

Also, for example, if the X-ray source is turned toward the movement direction of the X-ray photographing means along with the arcuate movement of the X-ray photographing means, a constant area of the X-ray flux can be emitted to the X-ray photographing means. As a result, a uniform X-ray flux can always be emitted to the subject without variation.

In the present invention, the X-ray photographing device is a photographing device which can photograph CT tomographic images, and the X-ray photographing means is a CCD sensor, and in the first photographing step, the shifting/photographing step executed following the above first photographing step, and the shifting/photographing step executed following the above shifting/photographing step, the X-ray flux is preferably detected while the X-ray photographing means is turned in the same direction in each photographing step.

According to the above structure, by detecting the X-ray flux in each photographing step along with turning of the X-ray photographing means in the same direction, the CCD sensor can be adopted as the X-ray photographing means.

In the present invention, the X-ray photographing device is a photographing device which can photograph CT tomographic images, and the X-ray photographing means is a CMOS sensor or a CdTe sensor, and, in the first photographing step, and the shifting/photographing step executed following the above first photographing step, the X-ray flux is detected while the X-ray photographing means is turned in the direction opposite to each other. Likewise, in the shifting/photographing step, and the shifting/photographing step executed following the above shifting/photographing step, the X-ray flux is detected while the X-ray photographing means is turned in the direction opposite to each other. In this way, in one photographing step and other photographing step executed following the one photographing step, the X-ray flux is preferably detected while the X-ray photographing means is turned in the direction opposite to each other.

According to the above structure, in one photographing step and other photographing step executed following the above one photographing step, by detecting the X-ray flux along with turning the X-ray photographing means in the direction opposite to each other in each photographing step, the CMOS sensor or the CdTe sensor (direct conversion type semiconductor detecting element) can be adopted as the X-ray photographing means.

In the present invention, the turning means preferably has a turning arm and a turning/driving means for turning the turning arm, the supporting member comprises an arcuate movement arm axially supported by the arcuate movement center axis of the turning arm, the arcuate movement means for arcuately moving the arcuate movement arm is provided on the turning arm so as to turn the turning arm by the turning/driving means, so that the arcuate movement arm is turned so as to turn the X-ray source and the X-ray photographing means around the subject, and so that the arcuate movement arm is turned by the arcuate movement means so as to arcuately move the X-ray photographing means around the subject.

According to the above structure, the X-ray source and the X-ray photographing means are provided on the arcuate movement arm which is the supporting member, and the arcuate movement arm is axially supported by the arcuate movement center axis so that the X-ray source and the X-ray photographing means which are provided on the arcuate movement arm turned around the subject by the turning means, and so that the arcuate movement arm is turned by the arcuate movement means so as to arcuately move the X-ray photographing means around the subject.

In the present invention, the X-ray photographing device is preferably provided with an X-Y table for moving the supporting member freely in a two-dimensional plane, and the X-ray photographing device can photograph panoramic tomographic images in the photographing device.

According to the above structure, since the X-Y table allows the supporting member for supporting the X-ray source and the X-ray photographing means to move freely in the two-dimensional plane, the X-ray source and the X-ray photographing means can be moved along a predetermined panoramic photographing trajectory.

For this reason, the X-ray photographing device can be used as a panoramic photographing device for obtaining panoramic tomographic images.

In the present invention, a collimator for limiting the range of the X-ray flux emitted from the X-ray source is preferably provided opposite to the X-ray photographing means across the subject.

According to the above structure, by providing the collimator for limiting the range of the X-ray flux, an amount of scattered ray can be reduced. As a result, an image quality can be improved.

In the present invention, it is desirable that the arcuate movement means arcuately moves the collimator and the X-ray photographing means while keeping the X-ray source, the collimator, and the X-ray photographing means in alignment with each other.

According to the above structure, by arcuately moving the collimator and the X-ray photographing means while keeping the X-ray source, the collimator, and the X-ray photographing means in alignment with each other, a constant area of the X-ray flux is narrowed by the collimator so as to be emitted to the X-ray photographing means. As a result, a uniform X-ray flux can always be emitted to the subject efficiently without variation.

Also, the present invention provides an X-ray photographing device, comprising: an X-ray source for emitting X-ray flux to a subject; an X-ray photographing means for detecting the X-ray flux passing through the subject; a supporting member for supporting the X-ray source and the X-ray photographing means; a turning means for turning the supporting member to turn the X-ray source and the X-ray photographing means around the subject; a linear movement means for linearly moving the X-ray photographing means; and a control unit for controlling operations of the turning means and the linear movement means, wherein the control unit continuously executes a first photographing step of detecting the X-ray flux passing through the subject by the X-ray photographing means while the X-ray photographing means is moved within a first linear movement range by the linear movement means; a shifting/turning step of shifting/turning the supporting member around the subject by the turning means; and a shifting/photographing step of detecting the X-ray flux passing through the subject by the X-ray photographing means while the X-ray photographing means is moved within a second linear movement range by the linear movement means with the supporting member being shifted from the first linear movement range by an infinitesimal angle in the shifting/turning step, wherein the shifting/turning step and the shifting/photographing step are further executed sequentially following the shifting/photographing step.

According to the above structure, by detecting the X-ray flux passing through the subject while linearly moving the X-ray photographing means by the linear movement means, X-ray photographing means behaves as a two-dimensional X-ray photographing means within a range where the X-ray photographing means is linearly moved.

Accordingly, the present invention can realize an X-ray photographing device which can obtain CT tomographic images using an inexpensive X-ray photographing means having a relatively small rectangular detecting area, and can cut down costs efficiently.

Also, the present invention provides an X-ray photographing device, comprising: an X-ray source for emitting X-ray flux to a subject; an X-ray photographing means for detecting the X-ray flux passing through the subject; a supporting member for supporting the X-ray source and the X-ray photographing means; a turning means for turning the supporting member to turn the X-ray source and the X-ray photographing means around the subject; an X-ray moving means for arcuately or linearly moving the X-ray photographing means; and a control unit for controlling operations of the turning means and the arcuate movement means, wherein the control unit continuously executes a first turning/photographing step of detecting the X-ray flux passing through the subject by the X-ray photographing means while the X-ray source and the X-ray photographing means are turned around the subject by turning the supporting member by the turning means; a shift-moving step of arcuately or linearly moving the X-ray photographing means by an infinitesimal distance relative to the subject by the X-ray moving means; and a shift-turning/photographing step of detecting the X-ray flux passing through the subject by the X-ray photographing means while the X-ray source and the X-ray photographing means are turned around the subject by turning the supporting member by the turning means with the X-ray photographing means being shifted by an infinitesimal distance in the shift-moving step from a position of the X-ray photographing means in the first turning/photographing step; wherein the shift-moving step and the shifting/photographing step are further executed sequentially following the shift-turning/photographing step.

According to the above structure, since the shifting/photographing step is sequentially and repeatedly executed while the X-ray photographing means is shifted by the infinitesimal distance from the position of the X-ray photographing means in the first turning/photographing step by executing the shift-moving step and the shifting/photographing step sequentially from the first turning/photographing step and the shift-turning/photographing step, the X-ray photographing means behaves as a two-dimensional X-ray photographing means within a range where the X-ray photographing means is shifted for a plurality of times.

Accordingly, the present invention can cut down costs efficiently by realizing an X-ray photographing device which can obtain CT tomographic images using an inexpensive X-ray photographing means having a relatively small rectangular detecting area.

Effect of the Invention

The X-ray photographing device according to the present invention can obtain CT tomographic images using the inexpensive X-ray sensor having the relatively small rectangular detecting area, and can cut down costs efficiently.

BRIEF DESCRIPTION OF DRAWINGS

FIG. 3 is a plan view for explaining an operation of an arcuate movement of an X-ray sensor;

FIGS. 6A-6C are plan views for explaining an operation of photographing CT tomographic images when a CCD sensor is used as the X-ray sensor;

EMBODIMENTS FOR CARRYING OUT THE INVENTION

Figure 1B:
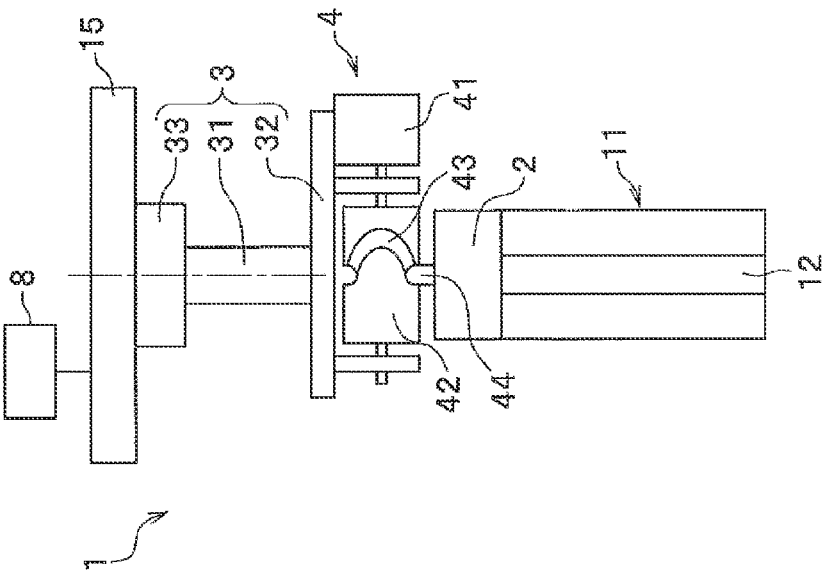
FIG. 1B is a side view conceptually showing the constitution of the X-ray photographing device according to the first embodiment of the present invention.

A first embodiment of the present invention will be explained in detail with reference to drawings.

As shown in FIG. 1, a dental X-ray photographing device 1 according to the first embodiment of the present invention comprises: an X-ray tube 11a which is an X-ray source 11; an X-ray sensor 12 which is an X-ray photographing means; a collimator 13 limiting a range of an X-ray flux L; an arcuate movement arm 2 which is a supporting member for supporting the X-ray source and the X-ray photographing means; a turning means 3 for turning the arcuate movement arm 2 around an arm turning center axis C1; an arcuate movement means 4 constructed of a cam mechanism for arcuately moving the X-ray sensor 12 around an arcuate movement center axis C2; an X-Y table 15 which can move freely in a two-dimensional plane; and a control unit 8 for controlling operations of the turning means 3 and the arcuate movement means 4 constructed of the cam mechanism.

In addition, although an application in dental field will be explained in this embodiment, the present invention is not limited to the dental field. The present invention can be widely applied to medical field, etc.

Also, the turning means 3 comprises: a turning arm 32 axially supported by a turning axis 31; and a turning/driving means 33 for turning the turning arm 32. Also, the turning means 3 turns the arcuate movement arm 2 so that the X-ray tube 11a and the X-ray sensor 12 are turned around a subject.

According to the above structure, by turning arm 32 using the turning/driving means 33 made of a servomotor, etc., the X-ray photographing device 1 turns the arcuate movement arm 2 so that the X-ray source 11 and the X-ray sensor 12 are turned around a subject K. Also, by turning the arcuate movement arm 2 using the arcuate movement means 4, the X-ray photographing device 1 arcuately moves the X-ray sensor 12 across the subject K.

Figure 1A:
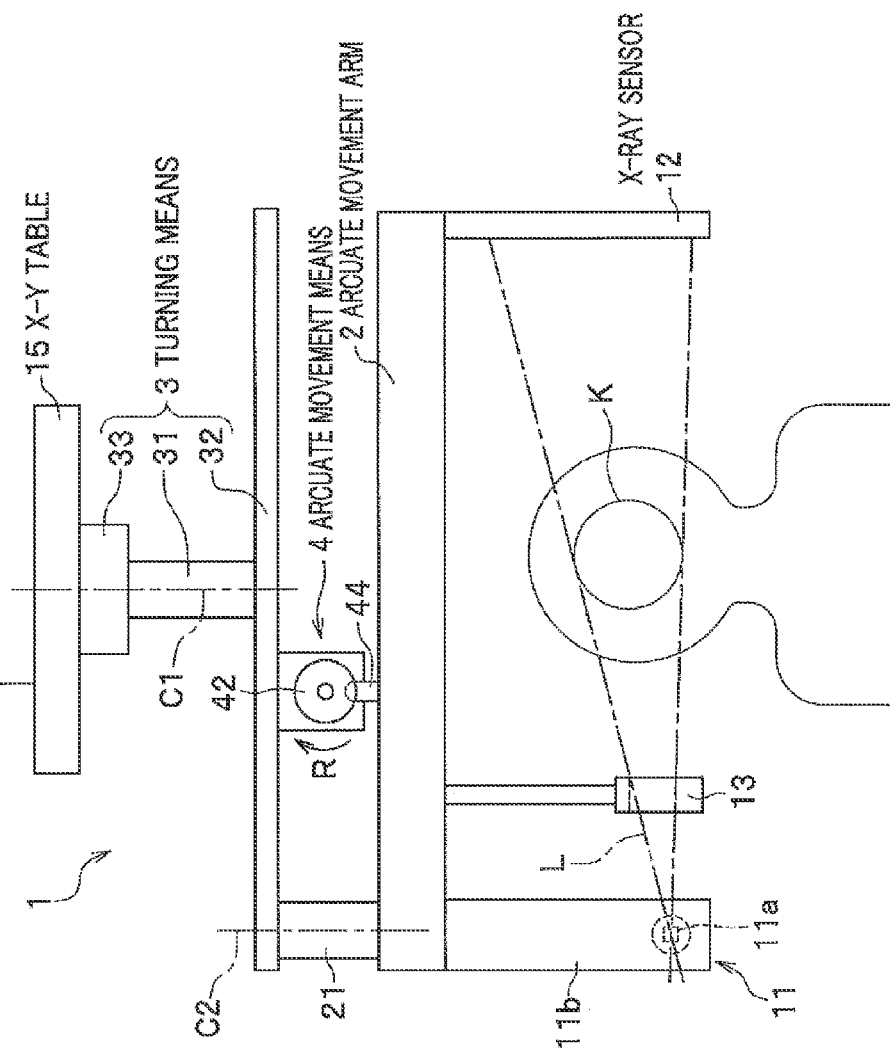
FIG. 1A is a front view conceptually showing a constitution of an X-ray photographing device according to a first embodiment of the present invention.

As shown in FIG. 1A, the X-ray source 11 is provided with the X-ray tube 11a for emitting an X-ray flux L to the subject K.

The X-ray tube 11a is attached to the supporting member 11b extending downwardly from the arcuate movement arm 2. For this reason, an emitting direction of the X-ray flux L emitted from the X-ray tube 11a is changed along with turning of the arcuate movement arm 2, and the X-ray sensor 12 is arcuately moved while synchronizing with the emitting direction of the X-ray flux L so as to follow it (see FIGS. 2A-2C).

Also, the arcuate movement arm 2 is provided with the collimator 13 for limiting the range of the X-ray flux L emitted from the X-ray tube 11a. The X-ray flux L narrowed by the collimator 13 passes the subject K, and is detected by the X-ray sensor 12 (see FIG. 2).

The X-ray sensor 12 detects the X-ray flux L passing through the subject K, and can be constructed of a CMOS sensor (see FIG. 5), a CCD sensor (see FIG. 6), a CdTe sensor, or other image sensors having a relatively narrow rectangular detecting areas (e.g., 6 mm wide).

For example, the CMOS sensor is characterized by its low cost and low power consumption, and the CCD sensor is characterized by its high-resolution. For this reason, an optimal image sensor can be chosen based on requirements for the X-ray photographing device.

The arcuate movement arm 2 is turnably and axially supported by an axial member 21 provided around the arcuate movement center axis C2. The arcuate movement center axis C2 is provided coaxially with the X-ray source 11 provided on the arcuate movement arm 2.

The X-ray source 11, the collimator 13, and the X-ray sensor 12 are provided to be collinear with one another on the arcuate movement arm 2.

For this reason, a constant area of the X-ray flux L emitted from the X-ray source 11 can be narrowed by the collimator 13 so as to be emitted to the X-ray sensor 12. As a result, a uniform X-ray flux L can always be emitted to the subject K efficiently without variation.

As shown in FIG. 1B, the arcuate movement means 4 constructed of the cam mechanism is provided with a cam roller 42 connected to a servomotor 41 to be turnably supported, a cam groove 43 formed on a circumferential surface of the cam roller 42, and a cam pin 44 accepted by the cam groove 43 so as to be moved along the cam groove 43.

The cam pin 44 is fixed to the arcuate movement arm 2 so as to project from the arcuate movement arm 2. Also, the arcuate movement means 4 constructed of the cam mechanism is provided on the turning arm 32 so that the cam pin 44 accepted by the cam groove 43.

Figure 2A:
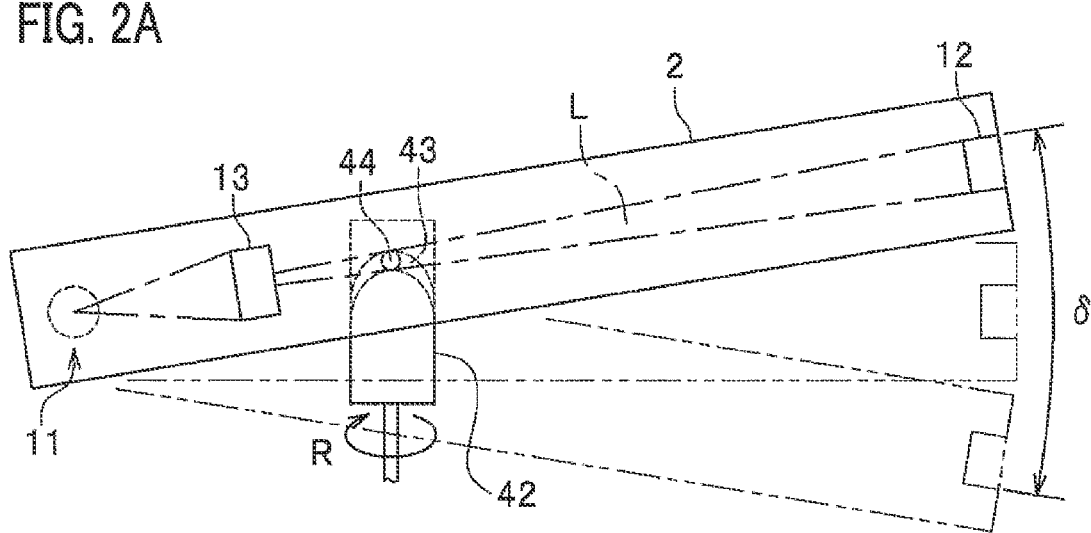
FIGS. 2A-2C are bottom views of a main part for explaining an operation of a arcuate movement means.

As shown in FIG. 2, according to the constitution, the cam roller 42 is turned by the servomotor 41 so that the arcuate movement arm 2 is turned around the arcuate movement center axis C2, and so that the X-ray sensor 12 is arcuately moved within an arcuate movement range δ (see FIG. 2A).

That is, when the cam roller 42 is turned, the cam pin 44 is moved in the direction where the cam pin 44 is orthogonal to the arcuate movement arm 2. By this movement of the cam pin 44, the arcuate movement arm 2 is arcuately moved within a range (the arcuate movement range δ) between a position shown in FIG. 2A and a position shown in FIG. 2C around the axial member 21 provided at the arcuate movement center axis C2.

Specifically, in a condition shown in FIG. 2C, the cam pin 44 is positioned below the cam roller 42, and the arcuate movement arm 2 is positioned at a lower side within the arcuate movement range. When the cam roller 42 is turned by 90 degrees in a right direction R (in clockwise direction in FIG. 1A) from this position, the cam pin 44 is moved to a central position shown in FIG. 2B along the cam groove 43, and the arcuate movement arm 2 is positioned at a center of the arcuate movement range δ (see FIG. 2B).

Figure 2B:
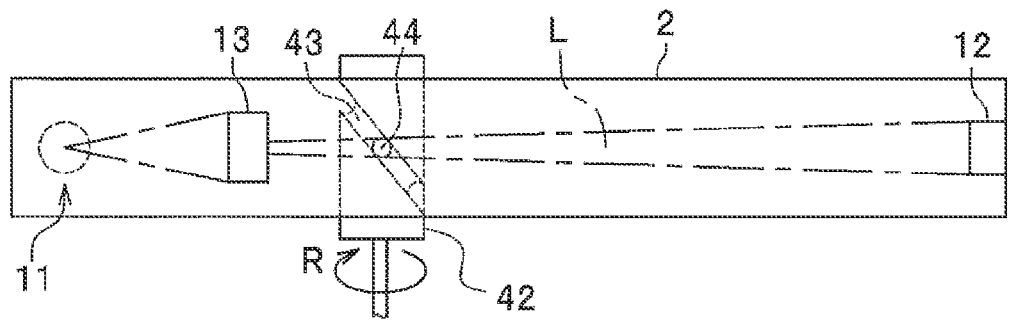
Figure 2C:
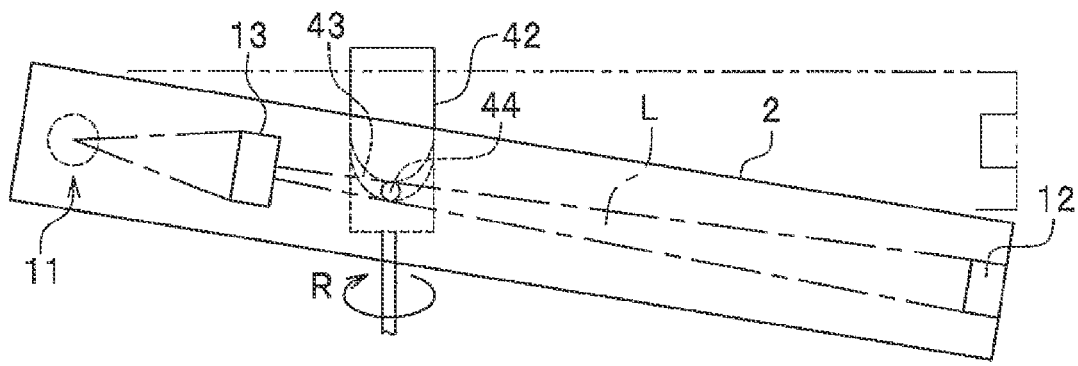

Also, when the cam roller 42 is further turned by 90 degrees in the right direction R from the central position shown in FIG. 2B, the arcuate movement arm 2 is moved to an upper side within the arcuate movement range δ shown in FIG. 2A.

In this way, by arcuately moving the arcuate movement arm 2 around the arcuate movement center axis C2, the collimator 13 and the X-ray sensor 12 provided on the arcuate movement arm 2 are arcuately moved as shown in FIG. 3 (see S2 and S3).

As described above, by detecting the X-ray flux L passing through the subject K while the arcuate movement means 4 arcuately moves the X-ray sensor 12 around the subject K within the arcuate movement range δ, the X-ray photographing device 1 according to this embodiment can behave as a two-dimensional X-ray photographing means within the arcuate movement range δ.

For this reason, by arcuately moving the X-ray sensor 12 having a relatively small rectangular detecting area (e.g., 6 mm wide), the X-ray photographing device 1 can behave as a wide-range two-dimensional X-ray photographing means for detecting the X-ray flux L within the arcuate movement range δ.

Also, by scanning the subject K while turning the X-ray sensor 12 which behaves as the wide-range two-dimensional X-ray photographing means by the turning means 3 around the subject K, CT tomographic images can be obtained.

In this way, the X-ray photographing device 1 can obtain CT tomographic images using the inexpensive X-ray sensor 12 having the relatively small rectangular detecting area, and can cut down costs efficiently.

The X-Y table 15 constructed of a linear movement guide (not shown) movably provided in an X-axis direction, and a linear movement guide (not shown) movably provided in a Y-axis direction which is orthogonal to the X-axis direction in a horizontal direction.

By providing the X-Y table 15, the arcuate movement arm 2 can move in parallel with a horizontal two-dimensional plane via the turning means 3, and the X-ray photographing device 1 can behave a photographing device which can obtain the CT tomographic images and the panoramic tomographic images.

That is, in the case where the X-ray photographing device 1 is used as the CT photographing device, the X-ray photographing device 1 can perform CT photographing by fixing the X-Y table 15 and the arm turning center axis C1. On the other hand, in the case where the X-ray photographing device 1 is used as a normal panoramic photographing device, the X-ray photographing device 1 can perform panoramic photographing by moving the arcuate movement arm 2 and the turning arm 32 in parallel with the horizontal two-dimensional plane as a unit by the X-Y table 15 on condition that the arcuate movement arm 2 is fixed without being arcuately moved.

With reference to FIG. 4, the other example of the arcuate movement means will be explained.

Figure 4A:
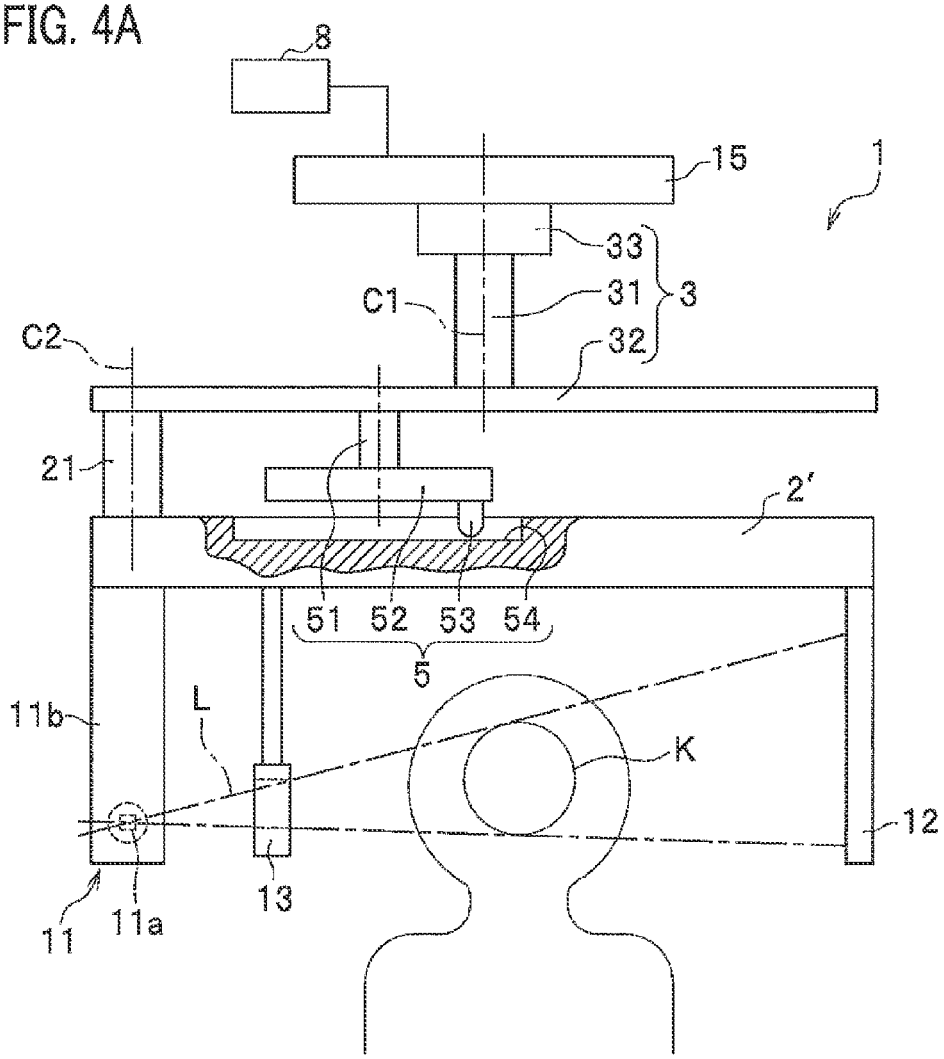
FIG. 4A is a front view showing a constitution of an arcuate movement means using a turning disk.

As shown in FIG. 4A, an arcuate movement means 5 constructed of a turning disk according to other example of the arcuate movement means comprises: a servomotor (not shown) axially supported by a turning arm 32; a turning axis 51 and a turning disk 52 which are connected to the servomotor; a driving pin 53 provided on the turning disk 52; and a guide groove 54 formed on an arcuate movement arm 2' so as to accept the driving pin 53.

Figure 4B:
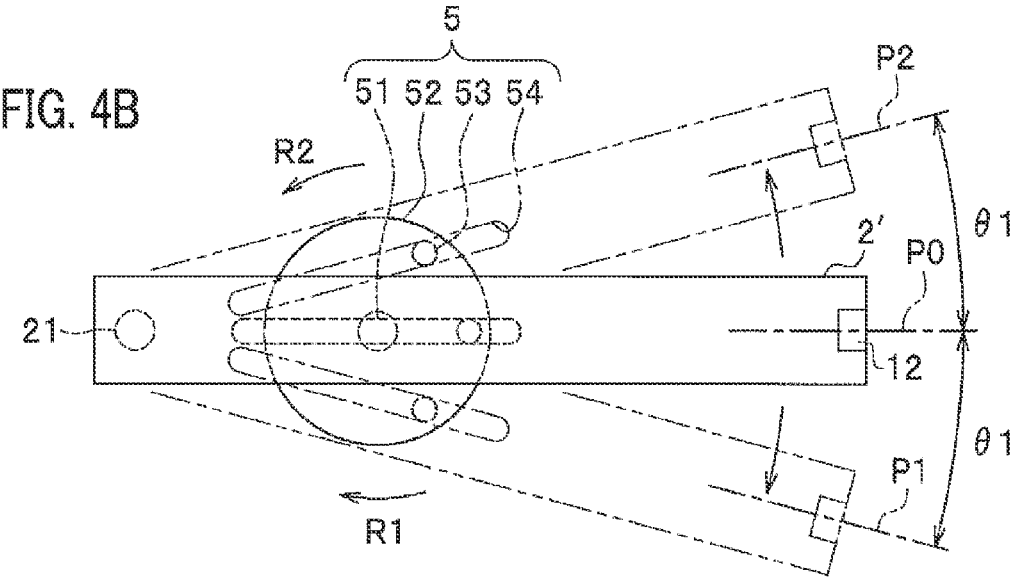
FIG. 4B is a bottom view showing the constitution of the arcuate movement means using the turning disk.

According to the above structure, as shown in FIG. 4B, in the arcuate movement means 5 constructed of the turning disk 52, if the turning disk 52 is turned by θ1 in clockwise direction R1, the arcuate movement arm 2' is arcuately moved from a central position P0 to a lower position P1. Likewise, if the turning disk 52 is turned by θ1 in a counterclockwise direction R2, the arcuate movement arm 2' is arcuately moved from the central position P0 to an upper position P2.

With reference to FIGS. 5 and 6, an operation of the X-ray photographing device 1 as constructed above will be explained. FIG. 5 is a plan view for explaining an operation in the case where the CT tomographic image are obtained using a CMOS sensor as the X-ray sensor. FIG. 6 is a plan view for explaining an operation in the case where the CT tomographic images are obtained using a CCD sensor as the X-ray sensor.

Here, in FIG. 5, the CMOS sensor can detect the X-ray flux L even if the CMOS sensor is turned in a counterclockwise (forward turn) direction or a clockwise (backward turn) direction. For this reason, in the case of the CMOS sensor, in photographing steps such as a second photographing step (the first photographing step and the following shifting/photographing step), or the second photographing step and a third photographing step (shifting/photographing step) which are alternately executed, turning directions which are reversed to each other (the forward turn and the backward turn) are combined.

For this reason, when the X-ray photographing device 1 obtains the CT tomographic images using the CMOS sensor, the first photographing step (see FIG. 5A) at which the CMOS sensor is forward turned in the counterclockwise direction within the first arcuate movement range $\delta 1$, the shifting/turning step (see FIG. 5B) at which the CMOS sensor is forward turned in the counterclockwise direction around the arm turning center axis C1, the second photographing step (shifting/photographing step) (see FIG. 5C) at which the CMOS sensor is backward turned in the clockwise direction within the second arcuate movement range $\delta 2$, the second shifting/turning step (see FIG. 5D) at which the CMOS sensor is forward turned in the counterclockwise direction around the arm turning center axis C1, and the third photographing step (shifting/photographing step) (see FIG. 5E) at which the CMOS sensor detects the X-ray flux L while the CMOS sensor is forward turned within a third arcuate movement range $\delta 3$, are sequentially executed.

Also, following the third photographing step (shifting/photographing step) (see FIG. 5E), the shifting/turning step and the shifting/photographing step, are further executed sequentially. In this way, for example, the CT tomographic images are obtained at each photographing step (first photographing step, second photographing step, ..., and $n_{th}$ photographing step) within each of the arcuate movement ranges $\delta 1$, $\delta 2$, ..., and $\delta n$ while the CMOS sensor is turned by 180 degrees or 360 degrees around the subject K.

Figure 5A:
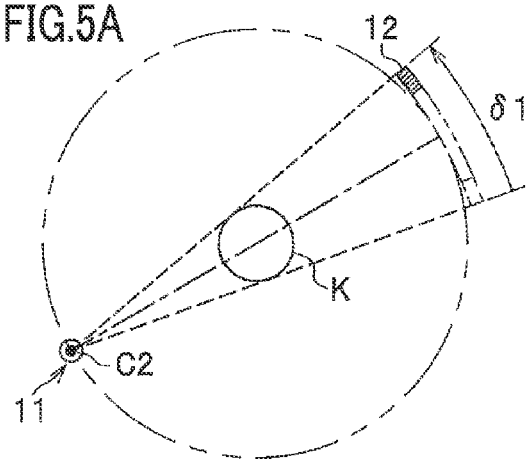
FIGS. 5A-5E are plan views for explaining an operation of photographing CT tomographic images when a CMOS sensor is used as an X-ray sensor.

Specifically, as shown in FIG. 5A, the X-ray sensor 12 detects the X-ray flux L passing through the subject K while the X-ray sensor 12 is forward turned within the first arcuate movement range $\delta 1$ around the arcuate movement center axis C2 by the arcuate movement means 4 (see FIG. 1) or the arcuate movement means 5 (see FIG. 4) at the first photographing step.

Figure 5B:
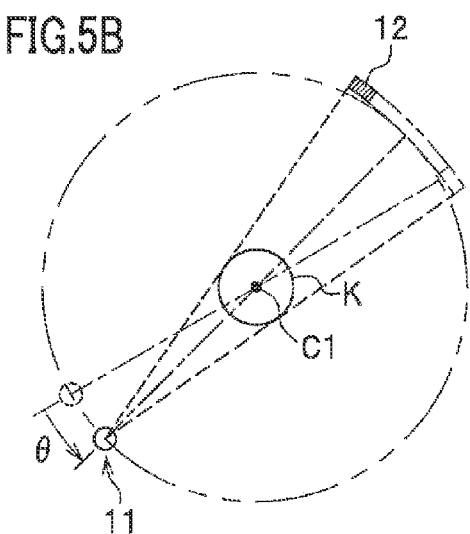

As shown in FIG. 5B, at the shifting/turning step, the arcuate movement arm 2 is forward turned in the counterclockwise direction by θ around the arm turning center axis C1 by the turning means 3 so that the X-ray source 11 and the X-ray sensor 12 are shifted/turned around the subject K.

Figure 5C:
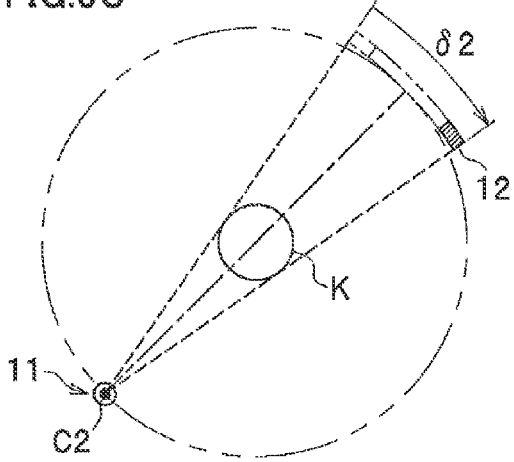

As shown in FIG. 5C, at the second photographing step, the X-ray sensor 12 detects the X-ray flux L passing through the subject K while the X-ray sensor 12 is backward turned around the arcuate movement center axis C2 within the second arcuate movement range $\delta 2$ by the arcuate movement means 4, 5 on condition that the X-ray sensor 12 is shifted from the first arcuate movement range $\delta 1$ by an infinitesimal angle θ at the shifting/turning step (see FIG. 5B).

Figure 5D:
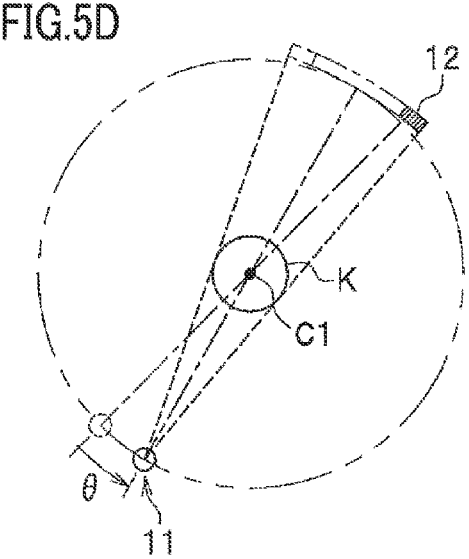
Figure 5E:
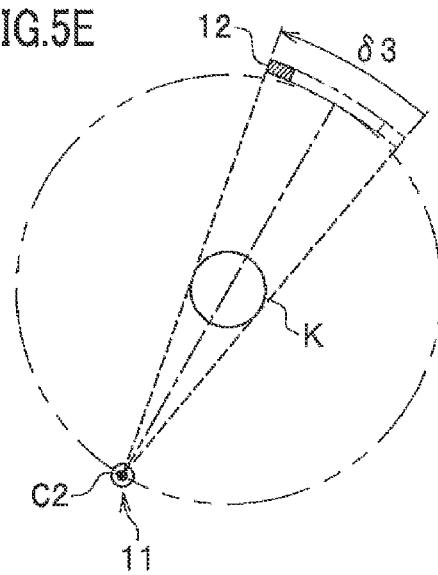

As shown in FIG. 5D, the second shifting/turning step is similar to the shifting/turning step shown in FIG. 5B. Also, as shown in FIG. 5E, the third photographing step is similar to the first photographing step shown in FIG. 5A.

Although the CMOS sensor is used in this embodiment (see FIG. 5), a CdTe sensor (direct conversion type semiconductor detecting element) may be used like the CMOS sensor since the CdTe sensor can detect the X-ray flux L like the CMOS sensor even if the CdTe sensor is turned in the counterclockwise (forward turn) direction or the clockwise (backward turn) direction. By using the CdTe sensor, a detection efficiency of the X-ray flux L can be improved.

Next, with reference to FIG. 6, an operation for obtaining the CT tomographic images in the case where the CCD sensor is used as the X-ray sensor 12 will be explained.

Here, the CCD sensor has a directivity in the movement direction, and can detect the X-ray flux L only in one direction. For this reason, the CCD sensor detects the X-ray flux L when the CCD sensor is turned in the same direction (i.e., when the CCD sensor is forward turned in the counterclockwise direction) at all photographing steps. Accordingly, for preparation of next photographing step executed following one photographing step, a backward step at which the CCD sensor is backward turned in the clockwise direction within the same arcuate movement range $\delta$ is included.

For this reason, when the X-ray photographing device 1 obtains the CT tomographic images using the CCD sensor, the first photographing step (see FIG. 6A) at which the CCD sensor is forward turned in the counterclockwise direction within a first arcuate movement range $\delta 11$, a backward step (see FIG. 6B) at which the CCD sensor is backward turned in the clockwise direction within the same first arcuate movement range $\delta 11$, the shifting/turning step (see FIG. 6B') at which the CCD sensor is forward turned in the counterclockwise direction around the arm turning center axis C1, and the second photographing step (shifting/photographing step) (see FIG. 6C) at which the CCD sensor is forward turned in the counterclockwise direction within the second arcuate movement range $\delta 12$, are sequentially executed.

In addition, although the shifting/turning step (see FIG. 6B') is executed following the backward step (see FIG. 6B) in this embodiment, the present invention is not limited to this. The backward step (see FIG. 6B) may be executed following the shifting/turning step (see FIG. 6B'), or the backward step (see FIG. 6B) may be executed while the shifting/turning step (see FIG. 6B') is executed.

Also, following the second photographing step (see FIG. 6C), the backward step ᄂ (see FIG. 6B) at which the CCD sensor is backward turned in the clockwise direction within the same second arcuate movement range $\delta 12$, and the shifting/turning step (see FIG. 6B') at which the CCD sensor is forward turned in the counterclockwise direction around the arm turning center axis C1, are further executed sequentially. In this way, the CT tomographic images are obtained at each photographing step (first photographing step, second photographing step, ..., and $n_{th}$ photographing step) within each of the arcuate movement ranges $\delta 11$, $\delta 12$, ..., and $\delta 1n$ while the CCD sensor is turned by 180 degrees or 360 degrees around the subject K.

In addition, since operations of the photographing step and the shifting/turning step are the same as those in the case of the CMOS sensor, the explanation will be omitted.

Figure 7:
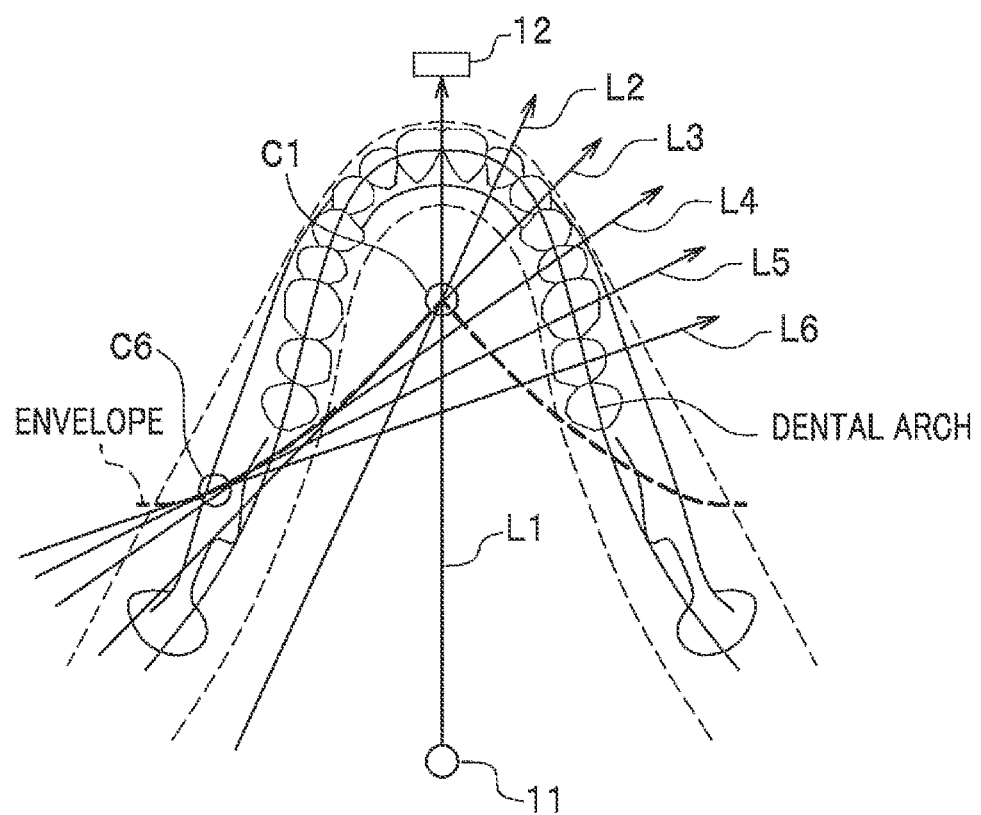
FIG. 7 is a plan view for explaining an operation when an X-ray photographing device according to the first embodiment of the present invention is used as a panoramic photographing device.

Next, with reference to FIG. 7, an operation for obtaining the panoramic tomographic images in the X-ray photographing device 1 will be explained. FIG. 7 is a plan view for explaining an operation in the case where the X-ray photographing device according to the embodiment of the present invention is used as the panoramic photographing device.

The X-ray photographing device 1 may be used as the panoramic photographing device since the X-Y table 15 drives the arcuate movement arm 2 and the turning arm 32 as a unit without driving the arcuate movement means 4, and the arcuate movement arm 2 and the turning arm 32 are moved freely on a horizontal two-dimensional plane as the unit.

As shown in FIG. 7, when the panoramic tomographic images are obtained, the X-ray source 11 and the X-ray sensor 12 are turned around the subject K (see FIG. 1) with a center at the arm turning center axis C1 (see FIG. 1) by the turning means 3 (see FIG. 1) while the turning axis 31 (see FIG. 1) is moved from C1 to C6 by the X-Y table 15 along an envelope so that X-ray fluxes L1-L6 are vertically emitted to a dental arch.

Although the first embodiment of the present invention has been explained, the present invention is not limited to the first embodiment, and any other modifications are possible.

Although the X-ray photographing device 1 according to the first embodiment is constructed so that the collimator 13 and the X-ray sensor 12 are provided to be collinear with one another on the arcuate movement arm 2 and the arcuate movement arm 2 is turned around the arcuate movement center axis C2, the present invention is not limited to this. For example, as shown in FIG. 8, an X-ray photographing device 1' may be constructed so that the collimator 13 is arcuately moved by an arcuate movement means 61, and the X-ray sensor 12 is arcuately moved by the arcuate movement means 62 while synchronizing with the collimator 13.

Figure 8:
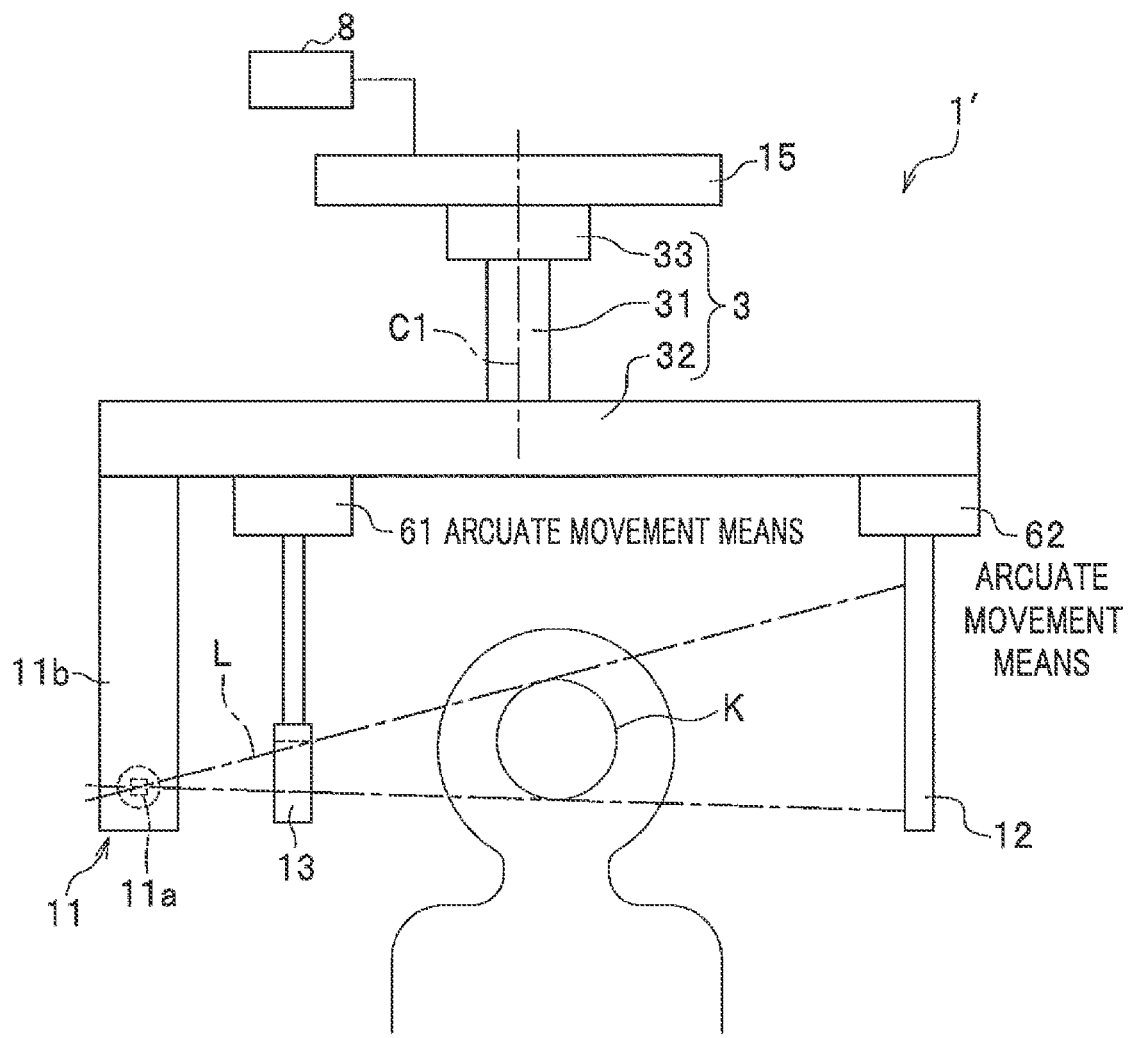
FIG. 8 is a front view showing an other embodiment of the arcuate movement means.

Also, in FIG. 8, the collimator 13 may be unified with the X-ray source 11, the X-ray source 11 unified with the collimator 13 may be arcuately moved by the arcuate movement means 61, and the X-ray sensor 12 is arcuately moved by the arcuate movement means 62 while synchronizing with the X-ray source 11.

Also, although the arcuate movement center axis C2 is provided coaxially with the X-ray source 11 in the first embodiment, the present invention is not limited to this. For example, the arcuate movement center axis C2 may be provided on a line joining the subject K and the X-ray sensor 12. Also, although the collimator 13 for limiting the range of the X-ray flux L is provided in this embodiment, the present invention is not limited to this. For example, the collimator 13 may be omitted in the present invention.

Also, although the X-ray source 11 is provided on the arcuate movement arm 2 and the X-ray source 11 is turned along with turning of the arcuate movement arm 2 in the first embodiment (see FIG. 1A), the present invention is not limited to this. For example, as shown in FIG. 9, the X-ray source 11 may be fixed to the turning arm 32.

Figure 9:
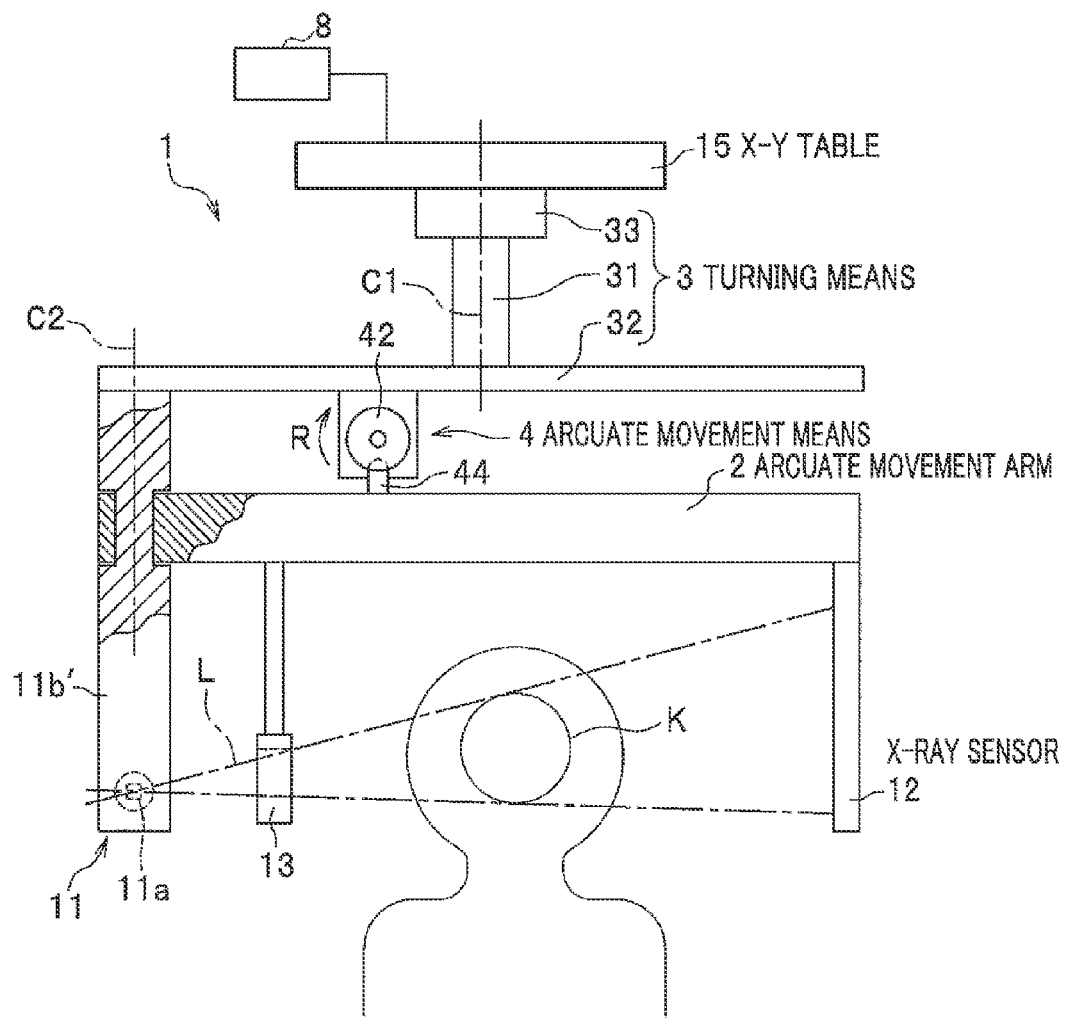
FIG. 9 is a front view showing an other example of an X-ray source.

That is, as shown in FIG. 9, the supporting member 11b' is fixed to the turning arm 32 and the X-ray tube 11a is attached to the supporting member 11b' in other example of the X-ray source 11. Also, the arcuate movement arm 2 is turnably and axially supported by the supporting member 11b'.

According to the above structure, since the X-ray tube 11a is not turned when the X-ray sensor 12 is arcuately moved by turning the arcuate movement arm 2 using the arcuate movement means 4, the X-ray source 11 can emit the X-ray flux L stably.

Figure 10:
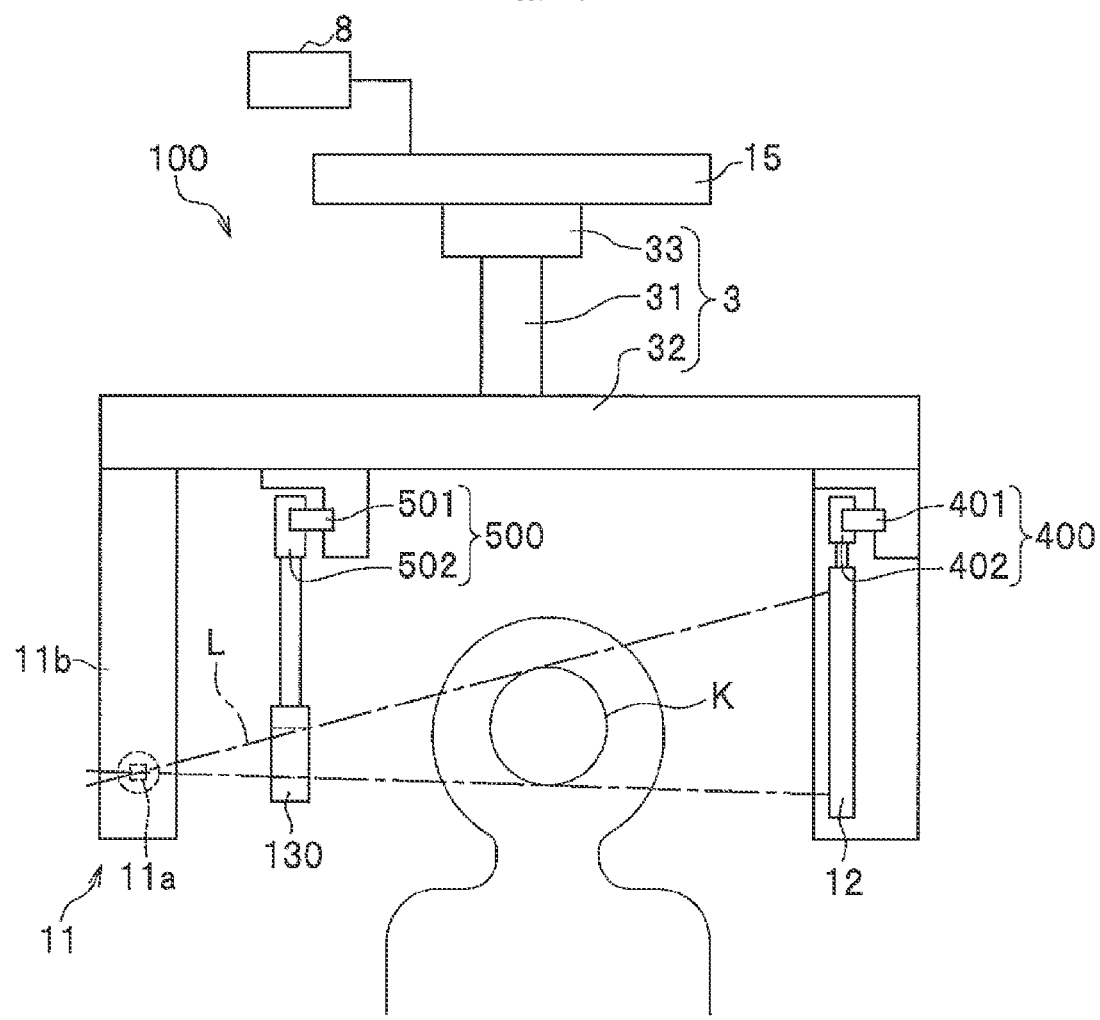
FIG. 10 is a front view of an example when a linear movement means is applied.

Also, although the X-ray sensor 12 is arcuately moved by the arcuate movement means 4, 5 in the first embodiment, the present invention is not limited to this. For example, the arcuate movement center axis C2 (see FIG. 1A) may be provided at a location far from the subject K. Specifically, as shown in FIG. 10, the above described arcuate movement means 4, 5, may be replaced with a linear movement means 400.

Hence, with reference to FIG. 10, an example in which the linear movement means 400 is applied to the X-ray photographing device 100 according to the present invention, will be explained.

The X-ray photographing device 100 according to the example to which the linear movement means 400 comprises: the linear movement means 400 for linearly moving the X-ray sensor 12; and a linear movement means 500 for linearly moving a collimator 130 for limiting the range of the X-ray flux L emitted from the X-ray tube 11a. Also, the linear movement means 400, 500 are provided on the turning arm 32 respectively.

In addition, in this example, since other components than the linear movement means 400, 500 are the same as those of the example using the arcuate movement means 4, 5, detailed explanation will be omitted.

The linear movement means 400 comprises: a guide rail 401 provided along a direction in which a linear movement is performed; a holder 402 provided so as to reciprocate along the guide rail; and a driving unit such as a ball screw, etc (not shown) for reciprocating the holder 402. Since a constitution of the linearly movement means 400 is not limited, detailed explanation will be omitted.

Figure 11:
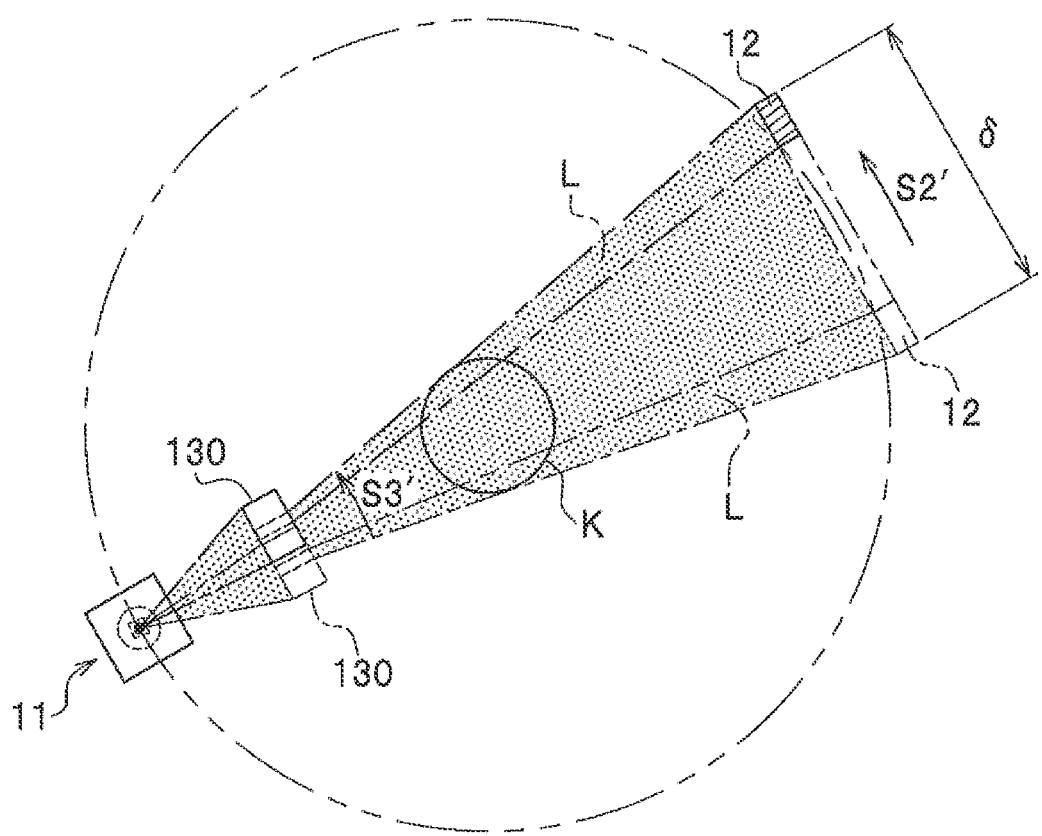
FIG. 11 is a plan view for explaining an operation of the example when the linear movement means is applied.

Also, likewise, the linear movement means 500 for linearly moving the collimator 130, comprises: a guide rail 501, and a holder 502, and the linear movement means 400 and the linear movement means 500 are controlled to be moved synchronized with each other (see S2' and S3' in FIG. 11).

In addition, although the linear movement means 500 is provided in this example, the present invention is not limited to this. For example, the collimator 130 may not be provided. If the collimator 130 is provided, the linear movement means 500 for linearly moving the collimator 130 may not be provided.

Next, with reference to FIG. 12, a second embodiment of the present invention will be explained.

In FIG. 12, only the control operation in the X-ray photographing device 1 according to the first embodiment of the present invention is modified, and other components such as the arcuate movement arm 2, the turning means 3, and the arcuate movement means 4, etc. are not modified. Therefore, only major differences are explained, and explanations for the same components are omitted.

In the above first embodiment, the X-ray sensor 12 detects the X-ray flux L while the X-ray sensor 12 is turned within the first arcuate movement range δ1 by the arcuate movement means 4, the X-ray sensor 12 detects the X-ray flux L while the X-ray sensor 12 is turned within the second arcuate movement range δ2 by the arcuate movement means 4 on condition that the X-ray sensor 12 is shifted from the first arcuate movement range δ1 by the turning means 3 at the shifting/turning step, and the X-ray sensor 12 detects the X-ray flux L while the X-ray sensor 12 is sequentially turned by 360 degrees or 180 degrees by the turning means 3 (see FIG. 5).

Figure 12A:
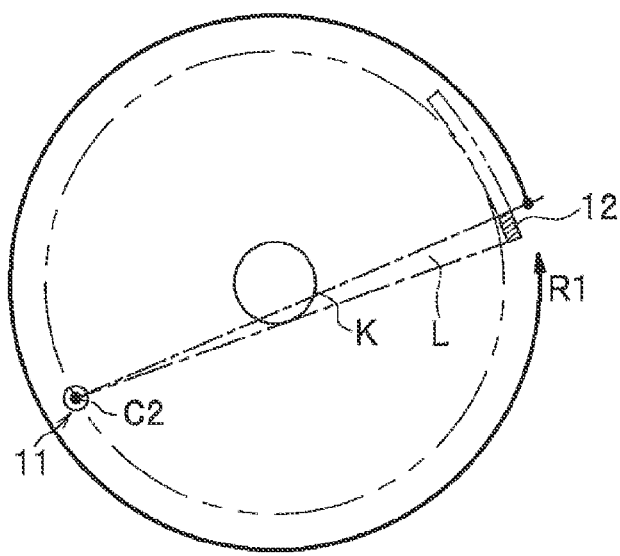
FIGS. 12A-12C are front views of a second embodiment of the present invention.
Figure 12B:
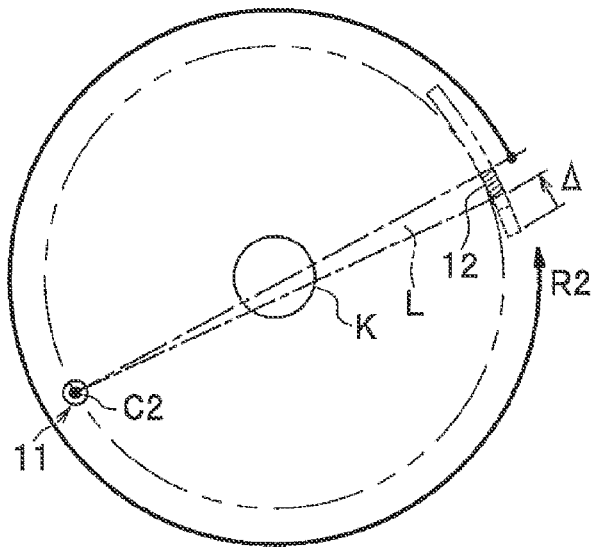

In contrast, in the control unit 8 according to the second embodiment, as shown in FIG. 12, a first turning/photographing step (see FIG. 12A) of detecting the X-ray flux L by turning the arcuate movement arm 2 (see FIG. 1) by 360 degrees R1 (or 180 degrees) by the turning means 3; a shift-moving step of shifting the X-ray sensor 12 by an infinitesimal distance Δ (see FIG. 12B) from the position of the X-ray sensor 12 at the first turning/photographing step; and a shift-turning/photographing step (see FIG. 12B) of detecting the X-ray flux L by turning the X-ray sensor 12 by 360 degrees R2 (or 180 degrees) by the turning means 3, are executed, and the shift-moving step and the shifting/photographing step are further executed sequentially following the shift-turning/photographing step.

Specifically, as shown in FIG. 12A, at the first turning/photographing step, the X-ray sensor 12 detects the X-ray flux L passing through the subject K while the arcuate movement arm 2 is turned by 360 degrees R1 for full reconstruction (or 180 degrees for half reconstruction) by the turning means 3 so that the X-ray source 11 and the X-ray sensor 12 are turned around the subject K (see FIG. 1).

As shown in FIG. 12B, at the shift-moving step, the arcuate movement arm 2 is turned by the arcuate movement means 4 (X-ray moving means), and the X-ray sensor 12 is arcuately moved around the arcuate movement center axis C2 (see FIG. 1) so that X-ray sensor 12 is shifted by the infinitesimal distance Δ relative to the subject K from the position of the X-ray sensor 12 at the first turning/photographing step.

As shown in FIG. 12B, at the shift-turning/photographing step, により the X-ray sensor 12 detects the X-ray flux L passing through the subject K while the arcuate movement arm 2 is turned by 360 degrees R2 for full reconstruction (or 180 degrees for half reconstruction) by the turning means 3 so that the X-ray source 11 and the X-ray sensor 12 are turned around the subject K like the first turning/photographing step on condition that at shift-moving step the X-ray sensor 12 is shifted by the infinitesimal distance Δ from the position of the X-ray sensor 12 at the first turning/photographing step (see FIG. 1).

Here, a magnitude of the infinitesimal distance Δ is appropriately set depending on a resolution, etc., of the CT tomographic image necessary for photographing. A gap may be occurred between the position of the X-ray sensor 12 at the first turning/photographing step and the position of the X-ray sensor 12 at the shift-turning/photographing step, and the X-ray sensor 12 may be moved to be adjacent side-by-side, or may be shifted to be overlapped.

Figure 12C:
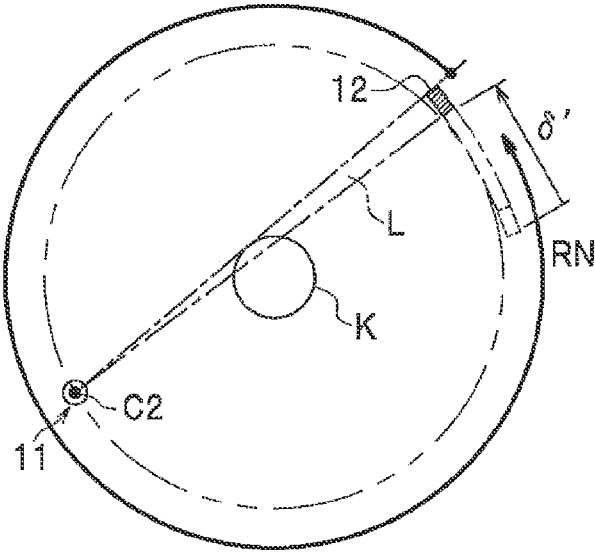

In this way, as shown in FIG. 12C, the control unit 8 (see FIG. 1) according to the second embodiment of the present invention further executes the shift-moving step and the shifting/photographing step sequentially following the shift-turning/photographing step.

That is, the control unit 8 (see FIG. 1) causes the X-ray sensor 12 to detect the X-ray flux L passing through the subject K while the control unit 8 causes the X-ray sensor 12 to be sequentially shifted by the infinitesimal distance Δ at the shift-moving step from the position of the X-ray sensor 12 at the first turning/photographing step to that at the $N_{th}$ shifting/photographing step (travel amount δ'), and causes the arcuate movement arm 2 to be turned by 360 degrees RN (or 180 degrees) using the turning means 3 so that the X-ray source 11 and the X-ray sensor 12 are turned around the subject K.

In addition, although the X-ray sensor 12 is arcuately moved by the arcuate movement means 4 in the second embodiment, the present invention is not limited to this. For example, the X-ray sensor 12 may be linearly moved by the linear movement means 400 shown in FIG. 10 (see FIG. 11).

DESCRIPTION OF REFERENCE NUMERALS 1, 1' X-RAY PHOTOGRAPHING DEVICE
2, 2' ARCUATE MOVEMENT ARM (SUPPORTING MEMBER)
3 TURNING MEANS
4, 5 ARCUATE MOVEMENT MEANS
8 CONTROL UNIT
11 X-RAY SOURCE
11A X-RAY TUBE
12 X-RAY SENSOR (X-RAY PHOTOGRAPHING MEANS)
13 COLLIMATOR
15 X-Y TABLE
21 AXIAL MEMBER
31 TURNING AXIS
32 TURNING ARM
33 TURNING/DRIVING MEANS
41 SERVOMOTOR
42 CAM ROLLER
43 CAM GROOVE
44 CAM PIN
51 TURNING AXIS
52 TURNING DISK
53 DRIVING PIN
54 GUIDE GROOVE
61, 62 ARCUATE MOVEMENT MEANS
80 CONTROL UNIT
400 LINEAR MOVEMENT MEANS
C1 ARM TURNING CENTER AXIS
C2 ARCUATE MOVEMENT CENTER AXIS
K SUBJECT
L X-RAY FLUX

The invention claimed is:

1. An X-ray photographing device, comprising:
an X-ray source for emitting an X-ray flux to a subject;
an X-ray photographing means for detecting the X-ray flux passing through the subject;
a supporting member for supporting the X-ray source and the X-ray photographing means;
a turning means for turning the supporting member to turn the X-ray source and the X-ray photographing means around the subject;
an arcuate movement means for arcuately moving the X-ray photographing means around the subject by turning the X-ray photographing means around an arcuate movement center axis provided on a line joining the subject and the X-ray photographing means; and
a control unit for controlling operations of the turning means and the arcuate movement means,
wherein the control unit continuously executes
a first photographing step of detecting the X-ray flux passing through the subject by the X-ray photographing means while the X-ray photographing means is turned around the arcuate movement center axis within a first arcuate movement range by the arcuate movement means;
a shifting/turning step of shifting/turning the supporting member around the subject by the turning means; and
a shifting/photographing step of detecting the X-ray flux passing through the subject by the X-ray photographing means while the X-ray photographing means is turned around the arcuate movement center axis within a second arcuate movement range by the arcuate movement means with the supporting member being shifted from the first arcuate movement range by an infinitesimal angle in the shifting/turning step,
wherein the shifting/turning step and the shifting/photographing step are further executed sequentially following the shifting/photographing step.

2. The X-ray photographing device according to claim 1, wherein the arcuate movement center axis is provided at a position where the X-ray source is provided.

3. The X-ray photographing device according to claim 1, wherein the X-ray photographing device is a photographing device which can photograph CT tomographic images, and the X-ray photographing means is a CCD sensor, and in the first photographing step, the shifting/photographing step executed following the above first photographing step, and the shifting/photographing step executed following the above shifting/photographing step, the X-ray flux is detected while the X-ray photographing means is turned in the same direction in each photographing step.

4. The X-ray photographing device according to claim 1, wherein
the X-ray photographing device is a photographing device which can photograph CT tomographic images, and
the X-ray photographing means is a CMOS sensor or a CdTe sensor, and,
in the first photographing step, and the shifting/photographing step executed following the above first photographing step, the X-ray flux is detected while the X-ray photographing means is turned in the direction opposite to each other,
in the shifting/photographing step, and the shifting/photographing step executed following the above shifting/photographing step, the X-ray flux is detected while the X-ray photographing means is turned in the direction opposite to each other, and
in one photographing step and other photographing step executed following the one photographing step, the X-ray flux is detected while the X-ray photographing means is turned in the direction opposite to each other.

5. The X-ray photographing device according to claim 1, wherein
the turning means has a turning arm and a turning/driving means for turning the turning arm,
the supporting member comprises an arcuate movement arm axially supported by the arcuate movement center axis of the turning arm,
the arcuate movement means for arcuately moving the arcuate movement arm is provided on the turning arm so as to turn the turning arm by the turning/driving means, so that the arcuate movement arm is turned so as to turn the X-ray source and the X-ray photographing means around the subject, and so that the arcuate movement arm is turned by the arcuate movement means so as to arcuately move the X-ray photographing means around the subject.

6. The X-ray photographing device according to claim 1, wherein
the X-ray photographing device is provided with an X-Y table for moving the supporting member freely in a two-dimensional plane, and
the X-ray photographing device can photograph panoramic tomographic images in the photographing device.

7. The X-ray photographing device according to claim 1, wherein a collimator for limiting the range of the X-ray flux emitted from the X-ray source is preferably provided opposite to the X-ray photographing means across the subject.

8. The X-ray photographing device according to claim 7, wherein the arcuate movement means arcuately moves the collimator and the X-ray photographing means while keeping the X-ray source, the collimator, and the X-ray photographing means in alignment with each other.

9. An X-ray photographing device, comprising:
an X-ray source for emitting X-ray flux to a subject;
an X-ray photographing means for detecting the X-ray flux passing through the subject;
a supporting member for supporting the X-ray source and the X-ray photographing means;
a turning means for turning the supporting member to turn the X-ray source and the X-ray photographing means around the subject;
a linear movement means for linearly moving the X-ray photographing means; and
a control unit for controlling operations of the turning means and the linear movement means,
wherein the control unit continuously executes
a first photographing step of detecting the X-ray flux passing through the subject by the X-ray photographing means while the X-ray photographing means is moved within a first linear movement range by the linear movement means;
a shifting/turning step of shifting/turning the supporting member around the subject by the turning means; and
a shifting/photographing step of detecting the X-ray flux passing through the subject by the X-ray photographing means while the X-ray photographing means is moved within a second linear movement range by the linear movement means with the supporting member being shifted from the first linear movement range by an infinitesimal angle in the shifting/turning step, wherein the shifting/turning step and the shifting/photographing step are further executed sequentially following the shifting/photographing step.

10. An X-ray photographing device, comprising:
an X-ray source for emitting X-ray flux to a subject;
an X-ray photographing means for detecting the X-ray flux passing through the subject;
a supporting member for supporting the X-ray source and the X-ray photographing means;
a turning means for turning the supporting member to turn the X-ray source and the X-ray photographing means around the subject;
an X-ray moving means for arcuately or linearly moving the X-ray photographing means; and
a control unit for controlling operations of the turning means and the X-ray moving means,
wherein the control unit continuously executes
a first turning/photographing step of detecting the X-ray flux passing through the subject by the X-ray photographing means while the X-ray source and the X-ray photographing means are turned around the subject by turning the supporting member by the turning means;
a shift-moving step of arcuately or linearly moving the X-ray photographing means by an infinitesimal distance relative to the subject by the X-ray moving means; and
a shift-turning/photographing step of detecting the X-ray flux passing through the subject by the X-ray photographing means while the X-ray source and the X-ray photographing means are turned around the subject by turning the supporting member by the turning means with the X-ray photographing means being shifted by an infinitesimal distance in the shift-moving step from a position of the X-ray photographing means in the first turning/photographing step;
wherein the shift-moving step and the shifting-turning/photographing step are further executed sequentially following the shift-turning/photographing step.

* * * * *